(12) United States Patent
Stiles

(10) Patent No.: US 7,794,999 B2
(45) Date of Patent: *Sep. 14, 2010

(54) CARNOBACTERIUM PISCICOLA CB1, CB2, AND CB3

(75) Inventor: Michael E. Stiles, Edmonton (CA)

(73) Assignee: CanBiocin, Inc., Edmonton, AB (CA)

( * ) Notice: Subject to any disclaimer, the term of this patent is extended or adjusted under 35 U.S.C. 154(b) by 1670 days.

This patent is subject to a terminal disclaimer.

(21) Appl. No.: 10/870,032

(22) Filed: Jun. 18, 2004

(65) Prior Publication Data

US 2005/0019458 A1    Jan. 27, 2005

(30) Foreign Application Priority Data

Jun. 20, 2003  (CA) ................................. 2432907

(51) Int. Cl.
  *C12N 1/00*  (2006.01)
  *C12N 1/12*  (2006.01)
  *A23B 4/12*  (2006.01)
  *A23L 1/31*  (2006.01)

(52) U.S. Cl. .................. 435/243; 435/252.1; 426/7; 426/55

(58) Field of Classification Search ............... 435/243, 435/252.9; 426/92, 652
See application file for complete search history.

(56) References Cited

U.S. PATENT DOCUMENTS

2003/0039632 A1 * 2/2003 Stiles et al. ................ 424/93.2

OTHER PUBLICATIONS

Campos, et al., 1997, Journal of Food Safety, 17, 151-160.*

* cited by examiner

*Primary Examiner*—Ruth A Davis
*Assistant Examiner*—Sheridan R Macauley
(74) *Attorney, Agent, or Firm*—William J. Bundren

(57) ABSTRACT

The compositions and methods of the present invention involve the use of certain bacteria and/or their fermentate products to treat foods, such as fresh and processed meat products.

6 Claims, 4 Drawing Sheets

Figure 1:
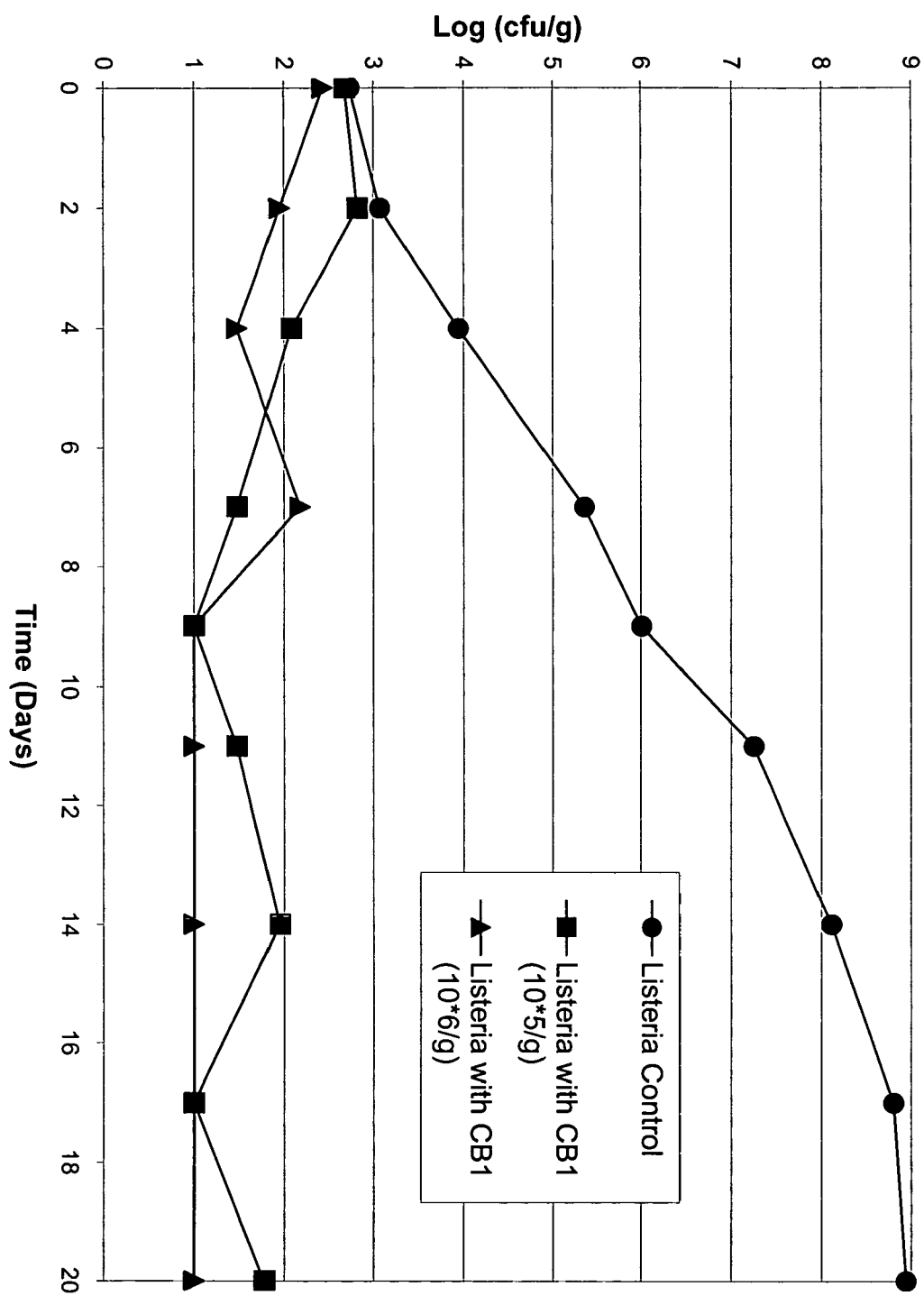

Growth of *Listeria monocytogenes* cocktail in the presence of *C. piscicola* CB1 on palcam in inoculated pork samples stored at 5 C for 20 days

CARNOBACTERIUM PISCICOLA CB1, CB2, AND CB3

I. FIELD OF THE INVENTION

This invention relates to novel strains of *Carnobacterium piscicola* that produce bacteriocin molecules having antimicrobial activity. In one particular application, the bacteria according to the invention is used as a food preservative. In another particular application, the bacteriocin and the bacterial strain that produces the bacteriocin is used to control *Listeria monocytogenes* ("*L. monocytogenes*") in meat products such as fresh sausages and vacuum-packed, processed meats, such as wieners, while not jeopardizing the storage life of the meats.

II. BACKGROUND OF THE INVENTION

There is a continual need for new food preservatives bearing new and useful properties. Further, there is growing interest in replacing traditional "chemical" food preservatives with effective "natural" preservatives, especially those that inhibit pathogenic microorganisms. In this regard, considerable research has been conducted on bacterial peptides, known as bacteriocins, that are often heat stable and have antimicrobial activity. Two such bacteriocins that are commercially produced for use as food preservatives are nisins A and Z and pediocin PA-1. Nisin has been given the status of Generally Recognized As Safe For Human Consumption (GRAS) by the United States FDA. Nisin and pediocin PA-1 have broad spectrum activities against gram-positive bacteria, affecting both pathogenic and spoilage microorganisms in food products.

Recent years have seen major advances in the development of microbial metabolites with antagonistic activities towards spoilage and pathogenic microorganisms associated with food. There now exists many antibacterial compounds, but only a few have been fully characterized and evaluated for food use. Additionally, consumer emphasis is now on minimally processed foods that are natural and preservative free. Because of this, there is considerable resistance to the use of chemical additives as food preservatives. Because of problems of antibiotic resistance, the use of antibiotics that can be used for therapeutic purposes may not be used for food preservation. Other biological inhibitors produced by microorganisms are currently being investigated for use in foods. Of particular interest are those antibacterial substances such as bacteriocins that are produced by Lactic Acid Bacteria ("LAB").

Bacteriocins, which are anti-bacterial peptides and proteins produced by LAB as normal by-products of their metabolism, are potentially very attractive natural preservatives. Many LAB are well-established, industrially important bacteria that include the genera *Lactococcus*, *Streptococcus*, *Pediococcus*, *Leuconostoc*, *Lactobacillus* and *Carnobacterium*. They have been used for the production of fermented foods that have been consumed safely for many decades. Given their status as "safe" microorganisms, they are a particularly suitable source of natural antimicrobials, such as bacteriocins, for use in foods.

Bacteriocins can have a broad or narrow spectrum of antibacterial activity, and they are not lethal to the cells that produce them. Bacteria protect themselves from the lethal effects of their own bacteriocins by the production of immunity proteins. There are distinct classes of bacteriocins produced by LAB:

A. Lantibiotics—which are small peptides of less than 5 kDa that contain unusual substituents, such as lanthionine, dehydroalanine, dehydrobutyrine and β-methyllanthionine. Examples include nisins A and Z, lacticins 481 and 3147, carnocin U149 and lactocin S.

B. Non-lantibiotic peptides—which are small peptides of 10 kDa or less and can be subdivided as follows: (i) listeria-active peptides e.g. pediocin PA-1, leucocin A and sakacin A.; (ii) poration complexes consisting of two proteinaceous peptides e.g. brochocin C and lactacin F.; and (iii) thiol-activated peptides requiring reduced cysteine residues for activity e.g. lactococcin B.

C. Large heat-labile proteins—which are larger proteins generally having a molecular weight greater than 31 kDa e.g. helveticin V-1829.

Notwithstanding the usefulness of the above described natural preservatives, a need still exists for lactic acid bacteria and their bacteriocins that are capable of controlling pathogenic and spoilage bacteria in specific food products.

III. SUMMARY OF THE INVENTION

This invention relates to novel strains of bacteriocin-producing *Carnobacterium piscicola* ("*C. piscicola*") having exceptional antimicrobial activities. Their unique characteristics are that they produce multiple bacteriocins, including at least the determinants for carnobacteriocin BM1 and piscicolin 126. These bacteriocins exhibit the following characteristics: i) they have broad spectrum anti-listerial activities; ii) they grow at refrigeration temperatures; and iii) they cause limited spoilage of the food relative to other similarly related spoilage microorganisms. The bacteriocins that these strains of *C. piscicola* produce have exceptional antimicrobial activities because of the unique combinations of bacteriocins produced. The combinations of bacteriocins can include carnobacteriocins BM1, A1 and B2, and piscicolin 126.

An embodiment of the present invention includes a method of treating fresh food by applying *C. piscicola*, its pasteurized or unpasteurized fermentate, or combinations thereof to the food. In these embodiments of the invention, the bacteria and its pasteurized or unpasteurized fermentate produce a predictable or controlled storage life.

In another embodiment of the present invention, the composition applied to the food comprises one or more natural bacterial culture(s), pasteurized or unpasteurized fermentate produced by the bacteria or combinations thereof. In preferred embodiments of the invention, the food is treated with the combination of the natural bacteria and its pasteurized or unpasteurized fermentate. In the most preferred embodiment of the invention, the food is treated with the combination of selected natural bacteria and a bacterial pasteurized or unpasteurized fermentate of a selected natural bacterial culture.

An embodiment of the present invention includes using a composition of the present invention to further protect a food product from the growth of gram positive pathogenic bacteria including, but not limited to, *L. monocytogenes*. The compositions of the present invention are effective against *L. monocytogenes* serotypes 1/2a, 1/2b, 3a and 4b.

The method of the present invention includes the use of one or more natural bacterial cultures, homologous pasteurized or unpasteurized fermentate, heterologous pasteurized or unpasteurized fermentate, or combinations thereof. The natural bacterial cultures of the present invention are described above. A homologous fermentate refers to the culture supernatant of a single bacteria culture prepared according to standard preparation techniques. A heterologous fermentate refers to the culture supernatant derived from a different bacterial culture prepared according to standard preparation techniques. The homologous or heterologous fermentate may be i) pasteurized or unpasteurized; ii) lyophilized; or iii) freeze dried. Two or more bacterial cultures may be mixed or added separately. Two or more fermentates may be mixed or added separately. A bacterial culture combined with one or more fermentates may be mixed, or added sequentially.

In another exemplary embodiment, the present invention consists in a biologically pure culture of bacterial strain CB1. A sample of bacterial strain CB1 has been deposited under the Budapest Treaty with the American Type Culture Collection as ATCC No. PTA-5313.

In another exemplary embodiment, the present invention consists in a biologically pure culture of bacterial strain CB2. A sample of bacterial strain CB2 has been deposited under the Budapest Treaty with the American Type Culture Collection as ATCC No. PTA-5314.

In another exemplary embodiment, the present invention consists in a biologically pure culture of bacterial strain CB3. A sample of bacterial strain CB3 has been deposited under the Budapest Treaty with the American Type Culture Collection as ATCC No. PTA-5315.

In another exemplary embodiment, the present invention comprises a method of preserving foods or beverages, the method comprising adding to the food or beverage an effective amount of a bacterial culture of the present invention, alone or in combination with a fermentate. The inventors have found that an amount of $10^2$, or less, colony forming units ("cfu") per gram or per cm$^2$ is typically not sufficient to compete with the existing adventitious microbial population. The inventor has found that about $10^3$ cfu per gram or per cm$^2$ is sufficient to overcome the growth of the existing adventitious bacterial population. One skilled in the art will recognize that the amount of adventitious bacteria in a food product is variable. In accordance with the present invention, the amount of the composition should be about ten times or more higher than the amount of adventitious spoilage or pathogenic bacteria.

In preferred embodiments of the invention, the method includes treating fresh meat. In the most preferred embodiments of the invention, the method includes treating or preserving fresh sausage or vacuum-packaged wieners.

The present invention also relates to the use of the bacterial composition and/or bacteriocin produced by the composition in the treatment of *Listeria*, to inhibit the growth of *Listeria* in meats.

The invention also relates to a fermentate comprising one or more bacteriocins produced by strains CB1, CB2, and/or CB3. In preferred embodiments of the invention, the fermentate comprises piscicolin 126, carnobacteriocin BM1, and an identifiable but uncharacterized proteinaceous compound(s) having antibacterial activity.

The bacteriocin of the present invention may be isolated from natural sources.

An advantage of the invention is unprecedented anti-listerial activity. Such a broad anti-listerial spectrum is unexpected and unusual. Another advantage of the invention is that there is both bacteriocidal and bacteriostatic potential. Yet another advantage of the invention is that these bacteria grow at temperatures as low as 0° C., which indicates that they grow and are effective under refrigeration temperatures that is essential for the preservation of meats. Yet a further advantage of the invention is that these strains do not cause significant spoilage of the meats in and of themselves. The first natural variant of the invention that, when used in combination with other bacteria or bacteriocins, shows substantial enhancement of antibacterial activities.

Given the following enabling description of the drawings, the invention should become evident to a person of ordinary skill in the art.

IV. BRIEF DESCRIPTION OF THE DRAWINGS

FIG. 1 is a graph of the anti-listerial activity of a composition of the present invention illustrating the reduction of bacterial numbers and the inhibition of a cocktail of four strains of *L. monocytogenes* in the presence of $10^3$ and $10^4$ cfu of *C. piscicola* CB1 inoculated per gram of pork sausage samples stored at 5° C. for greater than the proposed 15-day refrigerated storage life of the sausages.

Figure 2:
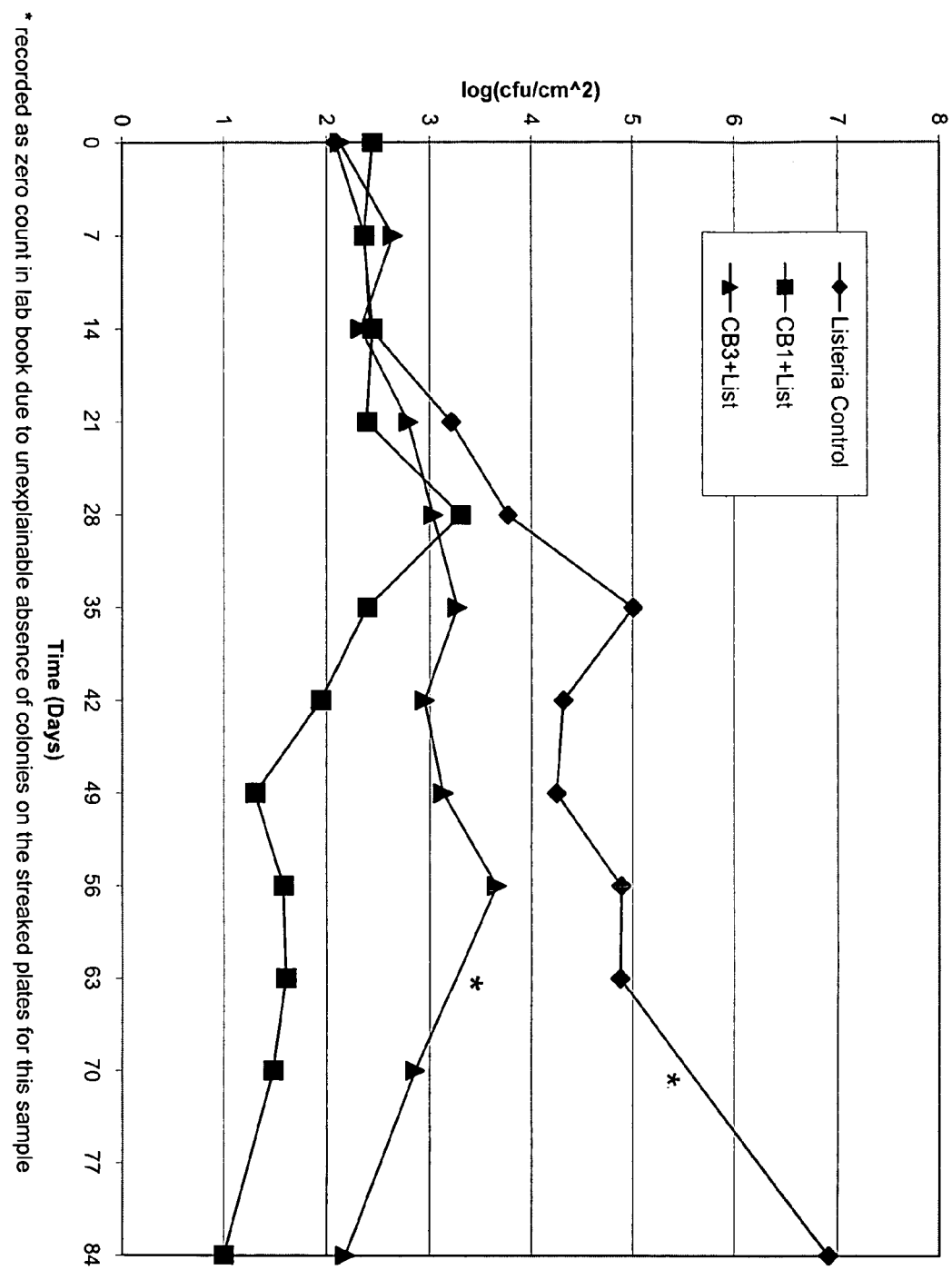

FIG. 2 is a graph of the first of three replicate trials illustrating the reduction of bacterial numbers and the inhibition of a cocktail of four strains of *L. monocytogenes* inoculated at $10^2$ to $10^3$ cfu per cm$^2$ in the presence of $10^4$ cfu of *C. piscicola* CB1 or CB3 per cm$^2$ on the surface of vacuum-packaged wieners stored at 5° C. over the 12-week refrigerated storage life of the product.

Figure 3:
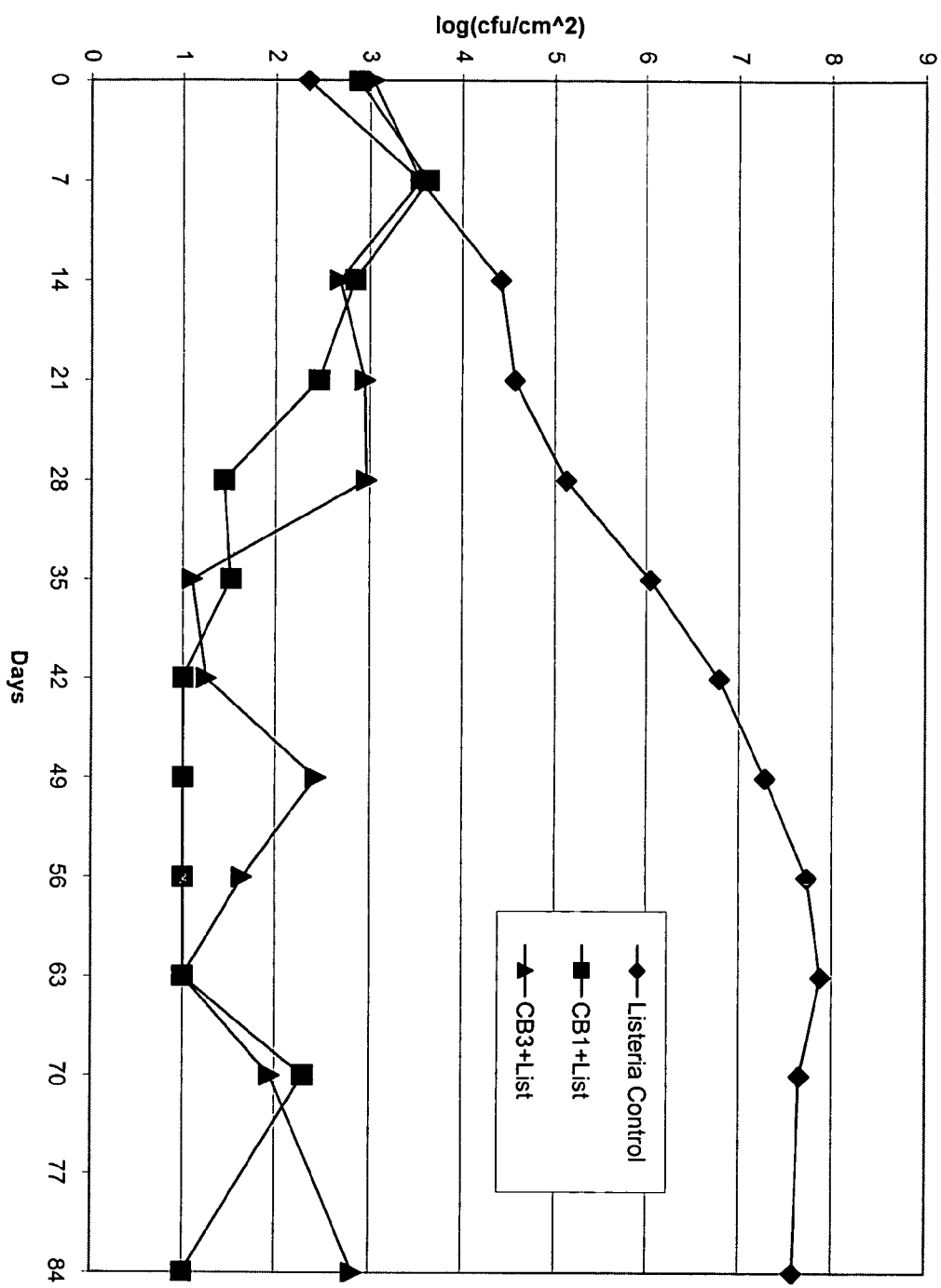

FIG. 3 is a graph of the second of three replicate trials illustrating the reduction of bacterial numbers and the inhibition of a cocktail of four strains of *L. monocytogenes* inoculated at $10^2$ to $10^3$ cfu per cm$^2$ in the presence of $10^4$ cfu of *C. piscicola* CB1 or CB3 per cm$^2$ on the surface of vacuum-packaged wieners stored at 5° C. over the 12-week refrigerated storage life of the product.

Figure 4:
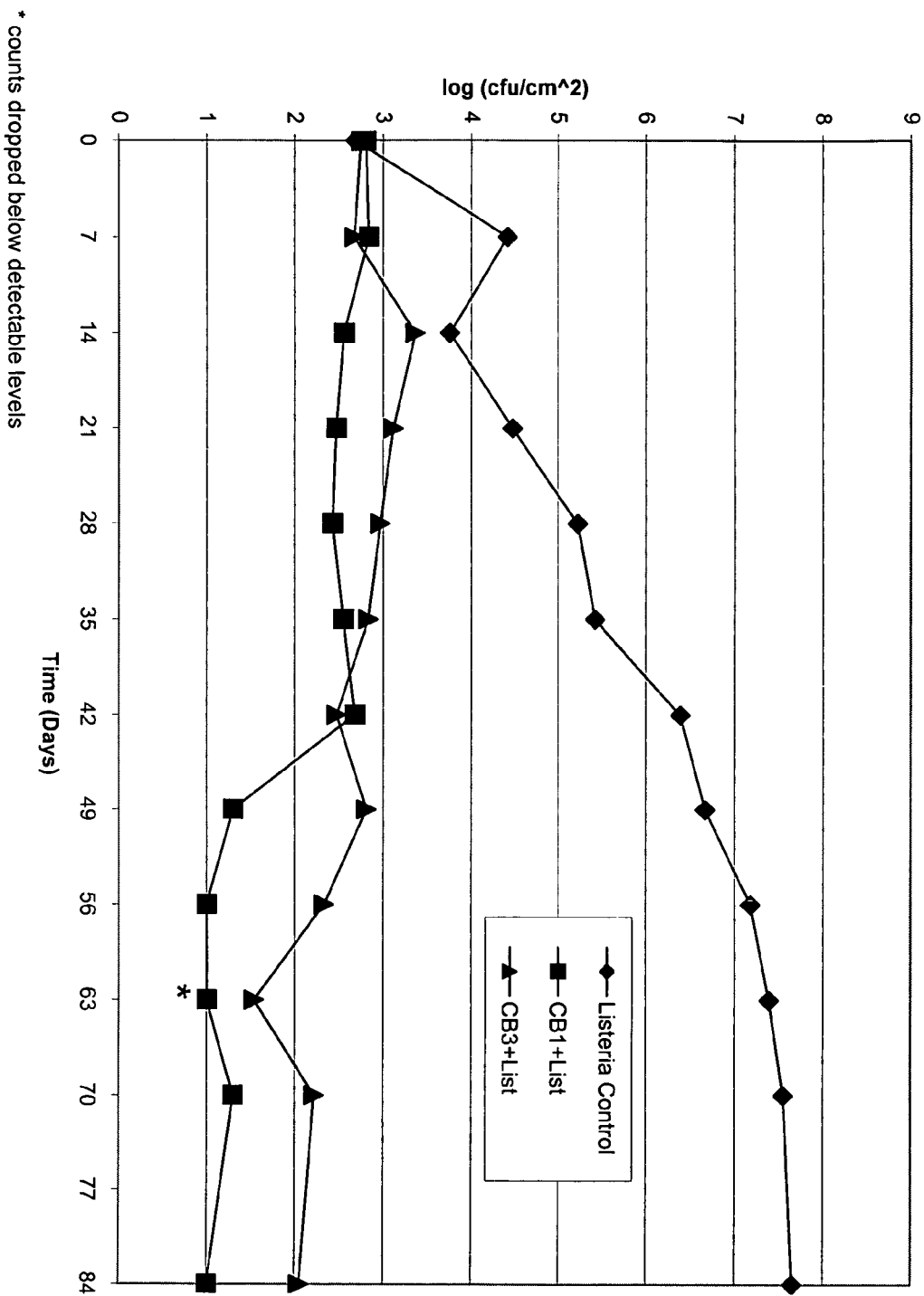

FIG. 4 is a graph of the third of three replicate trials illustrating the reduction of bacterial numbers and the inhibition of a cocktail of four strains of *L. monocytogenes* inoculated at $10^2$ to $10^3$ cfu per cm$^2$ in the presence of $10^4$ cfu of *C. piscicola* CB1 or CB3 per cm$^2$ on the surface of vacuum-packaged wieners stored at 5° C. over the 12-week refrigerated storage life of the product.

V. SPECIFIC DESCRIPTION OF THE INVENTION

A composition of the present invention includes strains of *Carnobacterium piscicola*, and each producing at least one, and typically three, bacteriocins. *C. piscicola* CB1 produces bacteriocins piscicolin 126, carnobacteriocin BM1, and another uncharacterized bacteriocin that exhibits antibacterial activity. *C. piscicola* CB2 produces piscicolin 126, carnobacteriocin BM1, and may produce one or more additional uncharacterized bacteriocins. *C. piscicola* CB3 produces piscicolin 126, carnobacteriocin BM1, and may produce one or more additional uncharacterized bacteriocins.

The compositions and methods of the present invention include the use of one or more natural bacterial cultures, homologous pasteurized or unpasteurized fermentate, heterologous pasteurized or unpasteurized fermentate or combinations thereof. The natural bacterial cultures of the present invention are described above. A homologous fermentate refers to the culture supernatant of a single bacterial culture prepared according to standard preparation techniques. A heterologous fermentate refers to the culture supernatant derived from a different bacterial culture prepared according to standard preparation techniques. The homologous or heterologous fermentate may be i) pasteurized or unpasteurized; ii) lyophilized; or iii) freeze dried. Two or more bacterial cultures may be mixed or added separately. Two or more fermentates may be mixed or added separately. A bacterial culture combined with one or more fermentates may be mixed, or added sequentially.

An important aspect of the present invention comprises the use of the bacterial fermentate in the preservation and treatment of fresh meats. In accordance with the teachings of the present invention, the bacteriocins produced by strains CB1, CB2, or CB3 appear to act synergistically to provide greater protection and effectiveness than use of the individual bacteriocins alone.

As used herein, fresh meat products refer to raw or uncooked meat (stored under refrigerated conditions) that may or may not contain additional spice mixtures, and includes integral or ground meat. Processed meat products refer to meats that have been i) formulated and cooked; ii) cured; or iii) uncured to produce a marketable product. "Fresh" and "processed" are intended to be used in their ordinary meaning as known to those skilled in the art. Typical meats include, but are not limited to, wieners, sausage, fish, and poultry.

The compositions and methods of the present invention may also be used to treat other food products including, but not limited to, modified atmosphere packaged vegetables, vacuum-packed pasta and fresh pasta products.

As used herein, predicted storage life refers to the capability of controlling spoilage for a discrete period, at which point spoilage becomes evident. For example, bacteria can be applied to a food product to attain a spoilage period of about 10 weeks, at which point spoilage occurs. Within the 10-week period, the composition of the present invention controls spoilage by one or more of the following ways: i) by applying bacteria having a known time to spoilage; ii) by applying bacteria that produces one or more proteins or bacteriocins that kill or control spoilage bacteria; or iii) by combinations thereof.

As used herein, enhanced safety refers to the inhibition of growth and/or the reduction of numbers of potentially pathogenic bacteria, ranging from bactericidal to bacteriostatic.

As used herein preservation of color refers to the extension of the time that the food product retains its desirable coloration. This concept is well known to those skilled in the art.

I claim:

1. An isolated *Carnobacterium piscicola* strain CB1, deposited in the ATCC as ATCC No. PTA-5313.

2. An isolated *Carnobacterium piscicola* strain CB2, deposited in the ATCC as ATCC No. PTA-5314.

3. An isolated *Carnobacterium piscicola* strain CB3, deposited in the ATCC as ATCC No. PTA-5315.

4. A method of treating a food product to inhibit the growth of *Listeria* comprising contacting the food product with a composition comprising one or more bacteria cultures selected from the group consisting of isolated *Carnobacterium piscicola* strains CB1 deposited in the ATCC under ATCC No. PTA-5313, CB2 deposited in the ATCC under ATCC No. PTA-5314, and CB3 deposited in the ATCC under ATCC No. PTA-5315.

5. A method of preparing processed meats comprising administering to the meat an effective amount of an isolated *Carnobacterium piscicola* strain selected from the group consisting of *Carnobacterium piscicola* strains CB1 deposited in the ATCC under ATCC No. PTA-5313, CB2 deposited in the ATCC under ATCC No. PTA-5314, and CB3 deposited in the ATCC under ATCC No. PTA-5315 wherein the effective amount is an amount effective to inhibit the growth of *Listeria*.

6. The method of claim 5 further comprising administering the strain in combination with a fermentate.

* * * * *